United States Patent [19]

Brook

[11] Patent Number: 4,658,649

[45] Date of Patent: Apr. 21, 1987

[54] ULTRASONIC METHOD AND DEVICE FOR DETECTING AND MEASURING DEFECTS IN METAL MEDIA

[75] Inventor: Mark V. Brook, West Hartford, Conn.

[73] Assignee: Combustion Engineering, Inc., Windsor, Conn.

[21] Appl. No.: 741,699

[22] Filed: Jun. 6, 1985

[51] Int. Cl.[4] .............................................. G01N 29/02
[52] U.S. Cl. ....................................... 73/624; 73/598
[58] Field of Search ................... 73/624, 628, 641, 642, 73/610, 612, 597, 598, 622, 637

[56] References Cited

U.S. PATENT DOCUMENTS

| | | | |
|---|---|---|---|
| 4,299,128 | 11/1981 | Gruber | 73/627 |
| 4,435,984 | 3/1984 | Gruber | 73/628 |
| 4,437,332 | 3/1984 | Pittaro | 73/624 |
| 4,522,064 | 6/1985 | McMillan | 73/628 |

*Primary Examiner*—Douglas A. Kreitman
*Attorney, Agent, or Firm*—Chilton, Alix & Van Kirk

[57] ABSTRACT

An non-destructive testing method employs an ultrasound generator which provides a beam having an axis which intersects the outer surface of an object to be tested at an angle relative to a line normal to the surface which is in the range of 23° to 28°. A longitudinal mode wave and a shear mode wave are propogated within the object and the shear wave is converted into longitudinal mode waves by reflection from an opposite surface of the object. The propogated and mode converted waves are reflected from different portions of a defect and the echos arrive serially in time at a receiver transducer. The ultrasound generator and receiver transducer are sonically isolated. The received signals have a favorable signal-to-noise ratio and the times of receipt thereof are employed to determine the dimensions of a detected defect.

16 Claims, 2 Drawing Figures

ULTRASONIC METHOD AND DEVICE FOR DETECTING AND MEASURING DEFECTS IN METAL MEDIA

BACKGROUND OF THE INVENTION

(1) Technical Field of the Invention

This invention relates generally to non-destructive testing methods and devices which are employed for detecting the presence and measuring the size of defects in metal parts. More particularly, this invention relates to methods and devices which employ ultrasonic energy for detecting and measuring cracks in, for example, the wall of a metal pipe.

While not limited thereto in its utility, the present invention is particularly well-suited to use in the nuclear industry. The safety of nuclear power facilities has become a matter of increasing public concern. A principal focus of this concern has been the integrity of the conduit systems employed to circulate coolant in nuclear power plants. Non-destructive testing to detect and examine cracks, which result from intergrannular stress corrosion or fatigue for example, originating at the inner diameter of clad or unclad piping of a nuclear system must be performed from the outside surface of the pipes and when the system is in service. Ultrasonic testing has proven to be the only viable approach to detecting cracks in such pipes while the system is in service.

Although ultrasonic testing has generally proven to be economically acceptable, previously employed ultrasonic techniques have been characterized by difficulty in accurately identifying false readings. Such difficulty often prevents the obtaining of reliable inspection results. The complex multiple refraction and back-scattering phenomena which is produced when a beam of ultrasonic energy is coupled into the wall of a metal pipe generally results in echos received at sensor (receiver) transducers having low signal-to-noise ratios which make interpretation of data very problematical and frequently less than reliable in terms of accurately identifying defects. The unfavorable signal-to-noise ratios make the obtaining of reliable information which could be employed for determining the dimensions of the located defects even more problematical. Accordingly, it is a principal aim of the present invention to provide a new and improved method and device for ultrasonic testing which results in a favorable signal-to-noise ratio of the test data.

(2) Prior Art

U.S. Pat. No. 4,435,984 discloses an ultrasonic multiple beam technique for detecting cracks in bi-metallic coarse grain materials. The patented method employs multiple beams, bands and pulses in addition to pulse shaping and beam forming, spectral and directional averaging and spacial filtering and pattern recognition. The method of U.S. Pat. No. 4,435,984 employs a pair of spaced transducers mounted at different angular orientations relative to a pipe to be inspected. In normal operation short shear wave pulses are serially propogated in the test object by the spaced transducers and an effort is made to analyze the echos received at the transducers to determine characteristic of any defects. A manual confirmation mode contemplated by the patentee included transmitting both longitudinal waves and shear waves toward a suspected defect.

BRIEF SUMMARY OF THE INVENTION

The present invention is a new and improved ultrasonic testing method and device which is characterized by echos having a very favorable signal-to-noise ratio which not only allows for a very reliable detection of cracks in metal piping but, most importantly, provides a reliable method for measuring the dimension of the detected cracks.

Briefly stated, the invention in a preferred form is an ultrasonic testing method and device for detecting defects in a metallic body having opposed surfaces such as, for example, the wall of a clad or unclad metal pipe. The method comprises propogating a beam of ultrasound energy in the pipe or other test object from a first location at an average angle of incidence relative to a line which is normal to the surface of the test object which lies in the range of 23° to 28° to thereby produce both a shear wave (S-wave) and a longitudinal wave (L-wave) in the pipe. The shear wave and the longitudinal wave have substantially equal amplitudes but different angles of refraction at the ultrasound transducer assembly-test object interface. The shear wave is reflected at the opposing interior surface of the test object and, in part, converted into a second longitudinal mode wave. Additionally, a "creeping" longitudinal wave which generally follows the contour of the interior surface of the test object is formed. The longitudinal wave and the mode converted L-waves, i.e., the second and "creeping" longitudinal waves, will encounter a region of interest in the test object. If the region of interest encompasses a defect, echoes of the longitudinal wave, the mode converted longitudinal wave and the "creeping" wave are reflected to and received at a second location. A a receiver transducer is positioned at the second location, which is adjacent to the first location and is oriented at an angle relative to a line normal to the surface of the test object which lies in the range of 12° to 28°. The time interval between receipt of the echoes of the longitudinal wave and both the mode converted longitudinal wave and the "creeping" wave are determined, and the dimensional extent of a defect in the region is determined in accordance with the determined time intervals. If the defect is a crack, the time between receipt of the echos commensurate with the propogated longitudinal wave and the "creeping" wave provides information of the real depth of the crack and thus may verify the information derived from the time interval between receipt of the echos commensurate with the propogated L-wave and the mode converted L-wave.

In accordance with the invention, a data base which relates time intervals to defect dimensions is employed to determine the dimensions of a crack or other defect. The transmitter and receiver are, in accordance with the invention, ultrasound transducers which are sonically isolated.

Apparatus in accordance with the invention comprises a first ultrasound transducer for generating a beam of ultrasonic energy. A mounting member is employed to mount the first transducer in spaced relationship relative to the test object so that the axis of the generated ultrasound beam intercepts the test object at an average angle of incidence in the range of 62° to 67°. A second transducer is employed to receive the echos reflected from abnormalities in the test object. A second mounting member is employed to mount the receiver transducer in spaced relationship to the test object and the ultrasound generator. The second mounting member orients the axis of the receiver transducer at an angle with respect to the normal to the surface of the test object of between 12° and 28°. An acoustic insulation material is interposed between the first and second mounting members to acoustically isolate the transducers. The first and second mounting members are preferably wedges of material having low sound attenuation characteristics such as, for example, Lucite plastic.

DETAILED DESCRIPTION OF THE INVENTION

Figure 1:
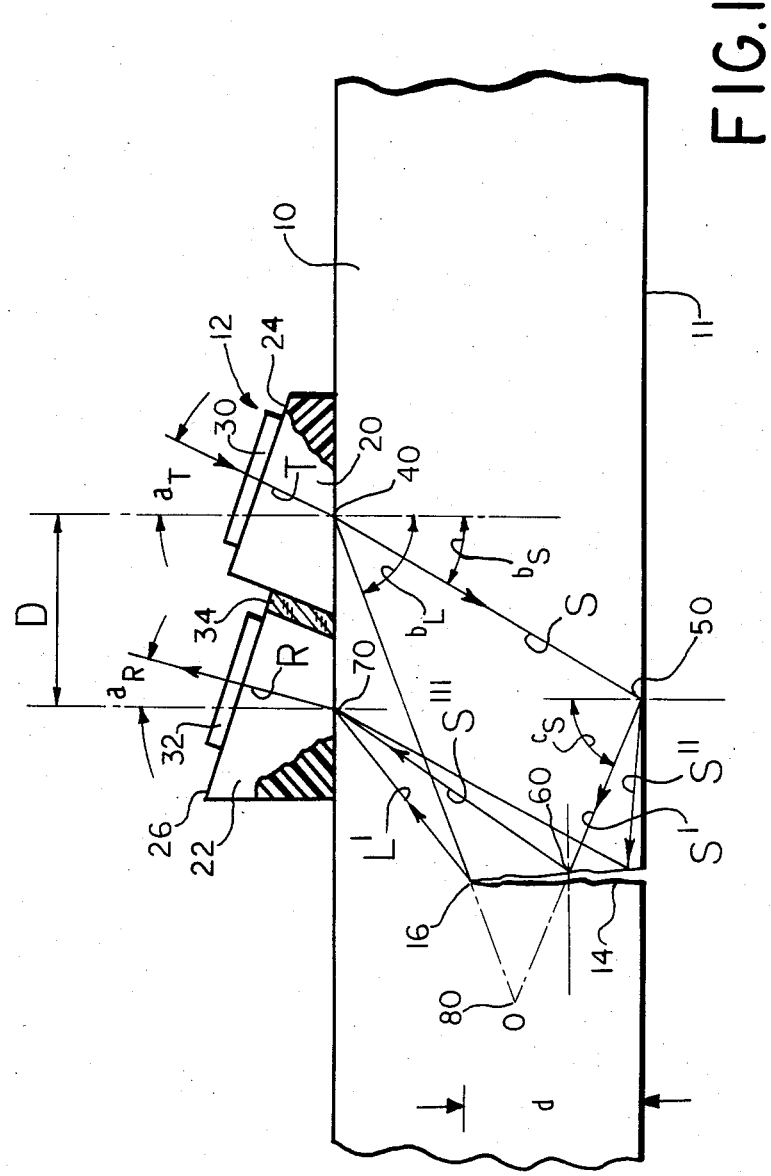
FIG. 1 is a side sectional view, partly broken away, partly in section and partly in schematic, illustrating an ultrasonic testing device and a pipe to be tested in accordance with the method and device of the present invention.

With reference to the drawing, an ultrasonic device for testing a pipe 10 is generally designated by the numeral 12. Ultrasonic device 12 may, for example, be employed for detecting cracks which form at the inner surface of pipe 10 and for measuring the depth of a detected crack. An exemplary crack is designated by the numeral 14 in the drawing. The ultrasonic device 12 is preferably employed for detecting flaws or defects in stainless steel pipes such as those employed in nuclear power facilities although the invention has numerous additional applications.

Ultrasonic device 12 comprises two platforms or shoes 20 and 22 which are adapted for positioning on the exterior surface of pipe 10 for selective longitudinal or axial movement therealong (to the right and left in FIG. 1) and for selective angular positioning about the central axis of the pipe. Shoes 20 and 22 are preferably formed of Lucite plastic material or other material having low ultrasound attenuation characteristics. Shoes 20 and 22 are provided with respective generally planar mounting surfaces 24 and 26. The surfaces 24 and 26 are spaced from the exterior surface of the pipe and have pre-established angular orientations relative thereto. Surface 24 is oriented at an angle of between 23° and 28° relative to a line which is normal to the exterior surface of pipe 10. Mounting surface 26 is oriented at an angle of between 12° and 28° relative to a line which is normal to the exterior surface of pipe 10. Pipe 10 will ordinarily have a thickness which ranges between 0.5 and 1.5 inches. The above-mentioned angles will be determined principally by the thickness of the test object and by the material from which the shoes 20 and 22 are constructed.

An ultrasound generator 30, i.e., a piezoelectric crystal, is mounted on surface 24 of shoe 20. Generator 30, when excited, generates a lobe-shaped beam of ultrasonic energy having an axis T which is normal to surface 24. A receiver crystal 32 is mounted on surface 26. Receiver 32 has an axis R which is normal to surface 26. A sound insulator 34 is disposed between shoes 20 and 22 for sonically isolating the receiver 32 from generator 30. Insulator 34 may, for example, be comprised of cork. The distance between the points wherein axes T and R respectively intersect the exterior surface of pipe 10 is given by distance D.

For purposes of illustrating the invention, crack 14 has been shown as a generally linear crack which extends substantially perpendicularly from the inside surface of pipe 10. Ultrasonic device 12 is selectively angularly and axially positioned relative to crack 14 so that the relationships illustrated in the drawing and further described below are obtained. It will be appreciated that ultrasonic device 12 and the ultrasonic testing method performed with the device provides a means for determining that the illustrated position is attained.

The beam produced by transducer 30 traverses axis T through the low attenuation medium of shoe 20 to impinge upon the exterior surface of pipe 10 at point 40. The angle of incidence of axis T to a line normal to the surface of pipe 10 at point 40 is designated by $a_T$. In order that the requisite wave mode conversion be obtained in accordance with the invention, it is critical that angle $a_T$ be less than a given critical angle $a_c$ determined by the constituent materials of shoe 20 and pipe 10 and the thickness of the pipe. In accordance with the invention, angle $a_T$ satisfies the following relationships:

$$23° \leq a_T \leq 28°$$

$$a_T < a_C$$

The ultrasonic beam is refracted at the interface between shoe 20 and the wall of pipe 10 into a longitudinal wave component initially traversing path L and a shear wave component initially traversing path S. The axis of the refracted shear S-wave defines an angle designated by $b_S$ relative to a line which is transverse to the surface of pipe 10. The axis of the refracted longitudinal L-wave defines an angle designated by $b_L$ relative to the same line normal to the surface of the pipe. It should be appreciated that the foregoing conversion of the generated beam of ultrasonic energy into the L-wave and S-wave components occurs only for the condition wherein angle $a_T$ is equal to or less than the critical angle $a_C$. The amplitudes of the L-wave and the S-wave are substantially equal.

The shear wave travels along path S until the wave front encounters interior surface 11 at point 50. The reflection of the shear wave from surface 11 results in a mode conversion to a longitudinal wave traversing path S' and a longitudinal wave which "creeps" along surface 11 as indicated by path S". The complement to the angle of reflection of the mode conversed longitudinal wave is given by $c_S$. The mode converted longitudinal wave traverses the pipe wall until the wave encounters the surface of crack 14 at point 60. The reflection of the mode converted wave from point 60 results in a longitudinal mode wave traversing the pipe wall along path S''' until the wave reaches point 70 at the interface between the exterior surface of pipe 10 and shoe 22. The echo is refracted at the pipe-shoe 22 interface at an angle of refraction $a_R$ so as to follow path R in shoe 22 for reception by receiver 32. The echo from point 60 of the crack is very well defined. In accordance with the invention angle $a_R$ satisfies the following relationship:

$$12° \leq a_R \leq 28°$$

The longitudinal L-wave which follows path L encounters the tip 16 of crack 14, is reflected along path L' to point 70, is refracted at the pipe-shoe 22 interface and travels through shoe 22 to receiver 32. The echo signal from tip 16 which arrives at receiver 32 is also very well defined.

The "creeping" wave, which follows the inner surface of the pipe 10 (indicated as path S″), is reflected from the base of the crack. A portion of the energy reflected from the base of the crack will arrive at the interface with shoe 22, be refracted and thus will be transduced by receiver 32 into an electrical signal.

It should be appreciated that in the absence of crack 14 the longitudinal component of the beam of ultrasonic energy and the mode converted longitudinal component thereof will intersect at point 80 as illustrated in the drawing. If a planar reflector were positioned at point 80, the longitudinal component of the beam would be reflected back to point 40. In addition, the mode converted longitudinal wave would be reflected by such a planar reflector back to point 50.

Receiver 32 will be connected, via amplification circuitry, to a display device (not illustrated) which has the capability of visually displaying the ultrasound energy inputs to the crystal. In accordance with the invention, receiver 32 is spaced a distance D from transmitter 30 and also sonically isolated from transducer 30 to improve the signal-to-noise ratio. The foregoing tandem transducer relationship improves the data commensurate with the energy reflected from tip 16 of crack 14 while causing a decrease in the magnitude of the echo from the side of the crack when compared to the conventional prior art ultrasound transducer transmitter/receiver configuration.

The arrival of the propogated shear wave at point 50 also results in a shear wave beam component (not illustrated) which is reflected from crack 14 to point 70 and is received by receiver 32. This echo does not effect the measurement.

Figure 2:
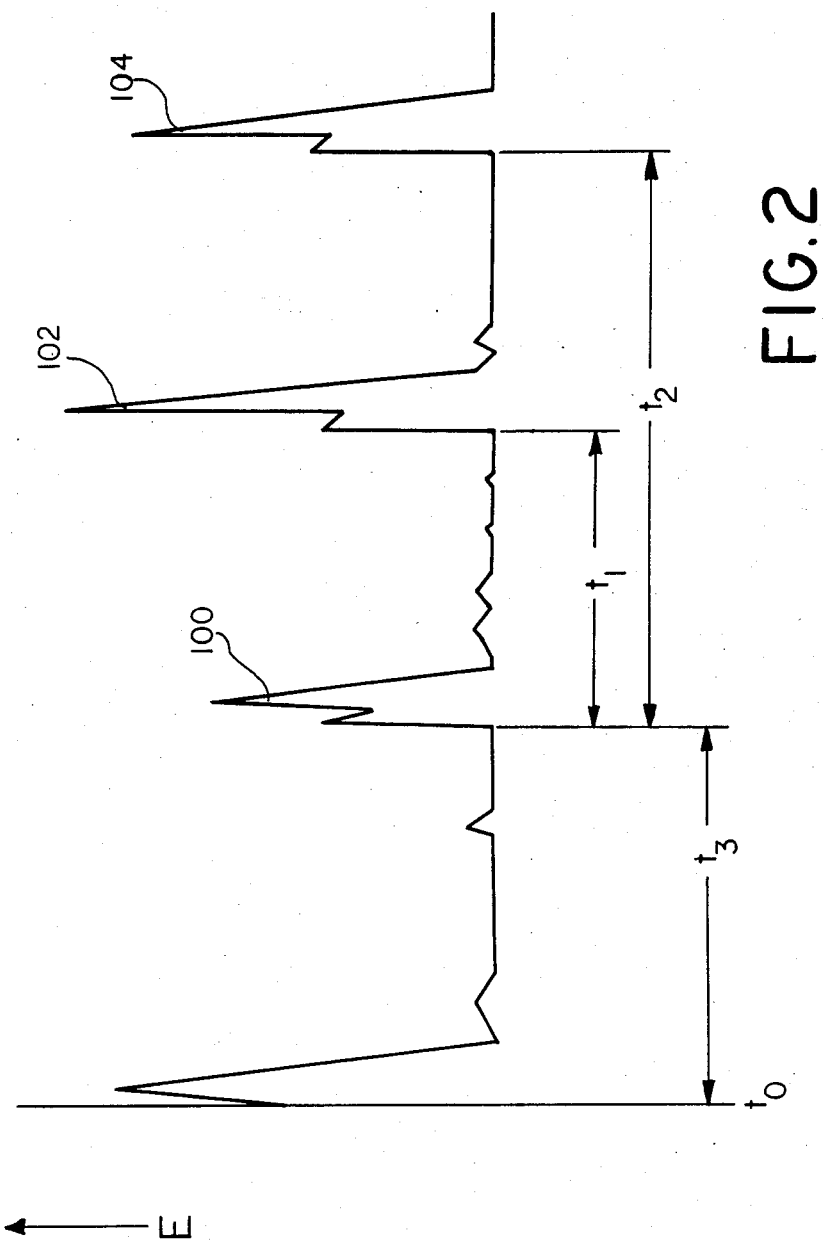
FIG. 2 is a graphical illustration of exemplary test data produced through use of the device of FIG. 1 in practicing the method of the invention.

It should be appreciated that the various echos arrive at receiver 32 at different times. In the event that the ultrasonic device 12 is positioned for probing a region of interest in which a crack occurs, the received echos assume the form of high energy, large amplitude signals which, when transduced to voltages by receiver 32, are generally as illustrated in FIG. 2. In FIG. 2 the vertical axis is the amplitude of the energy received and the horizontal axis is a time axis. The first signal designated by the numeral 100 represents the received energy E corresponding to the reflection of the L-wave from tip 16. The second signal designated by the numeral 102 represents the energy received by transducer 32 from the reflection of the ultrasonic beam at point 60. The time interval t between the occurrence of the first signal 100 and the second signal 102 is indicative of the distance between tip 16 and point 60 of the crack. The foregoing received echo signals are sufficiently well-defined so that the signals may be readily identifiable and the corresponding time intervals accurately determined. Through a test procedure, a relationship may be developed between the distance between tip 16 and point 60 and the corresponding time intervals $t_1$ so that the depth of a crack d may be measured by determining the time interval t between the reception of the corresponding echo signal pairs.

The signal commensurate with energy comprising the "creeping" wave reflected from the base of the crack is indicated at 104. The time $t_2$ between receipt of an echo from the tip of the crack and receipt of the echo from the base of the crack is commensurate with the actual crack depth. Thus, time delay $t_2$ may be utilized to verify the crack length measurement determined by reading crack length from a plot of length vrs. $t_1$ prepared by testing various wall thickness pipes with slots of different length formed therein.

The representation signals of FIG. 2 are typical of a test performed on an object having substantially parallel walls. The signals 102 and 104 corresponding to the echos of the mode-converted longitudinal waves will be partly lost if the wall surfaces are not parallel. If these signals become too small to be reliably usable, information as to the presence and location of an abnormality can be derived from the time between excitation of ultrasound generator 30 and the receipt of the echo from the tip of the crack, i.e., the time delay $t_3$. However, time $t_3$ by itself will not provide sufficient information to verify that the abnormality is in fact a crack. In the preferred situation, the walls of the test object are substantially parallel and all three echos represented by FIG. 2 are available.

In one example employing the foregoing device and method of the present invention, an ultrasonic device such as device 12 was successfully employed in connection with testing for cracks in a stainless steel pipe having a wall thickness of 1 inch. Slots of different depths were pre-formed on the inside of a sample pipe. An ultrasonic device 12 was sequentially moved along the exterior surface of the sample pipe so that a portion of interest of the pipe was tested. The signals generated by receiver 32 were displayed on a CRT, the displayed signals having very discernable peak amplitudes and echo signal pairs being easily identified.

The data from the test sample was employed to construct a data base from which the dimensions of actual defects were subsequently determined as a function of time intervals $t_1$ and $t_2$.

A particularly useful attribute of the present invention is that it allows testing at predetermined time intervals to determine if a known crack is growing. This is possible only with the technique of the invention because of the accurate measurements obtained therewith.

While a preferred embodiment of the foregoing invention has been set forth for purposes of illustration, the foregoing description should not be deemed a limitation of the invention herein. Accordingly, various modifications, alternatives and adaptations may occur to one skilled in the art without departing from the spirit and scope of the present invention.

What is claimed is:

1. A method for the measurement of abnormalities in a solid test object having opposed surfaces comprising the steps of:

intermittently transmitting a beam of ultrasonic energy from a first location so as to cause the axis of said beam to intercept a first surface of a test object at an angle in the range of 23° to 28° relative to a line normal to said first surface to thereby propogate a shear mode wave and a first longitudinal mode wave in said object, said waves having substantially equal amplitudes;

reflecting said shear mode wave at a second surface of said body which is disposed generally opposite to said first surface to convert a portion of the energy comprising said shear mode wave to a second longitudinal mode wave;

serially receiving echos of said propogated first and said second longitudinal mode waves as reflected from an abnormality within the test object, said echos being received at a second location on the test object first surface which is spaced from said first location, said echos being refracted at said first surface;

acoustically isolating said trasmitted beam prior to interception of the first surface of the test object thereby from said echos subsequent to refraction thereof;

measuring the time delay transmission of a pulse of ultrasonic energy which comprises the intermittently transmitted beam and receipt of the echo commensurate with the reflection of the propogated first longitudinal wave from the abnormality; and comparing the measured time delay with previously recorded data of time delay vrs. abonormality size to determine the distance from the test object first surface to the beginning of the abnormality.

2. The method of claim 1 wherein the steps of transmitting and receiving each include spacing a piezoelectric crystal from the first surface of the test object.

3. The method of claim 2 wherein the receiving piezoelectric crystal defines an axis which is oriented at an angle in the range of 12° to 28° relative to a line normal to the first surface of the object.

4. The method of claim 3 wherein the test object is a tubular member having substantially parallel inner and outer wall surfaces and wherein said first surface is the outer wall surface of the tubular member.

5. The method of claim 4 wherein the steps of spacing include mounting the piezoelectric crystals on members comprised of a material having low acoustic attenuation characteristics and coupling ultrasound energy to and from the crystals via the members.

6. The method of claim 3 wherein the steps of spacing include mounting the piezoelectric crystals on members comprised of a material having low acoustic attenuation characteristics and coupling ultrasound energy to and from the crystals via the members.

7. The method of claim 6 wherein the step of isolating includes positioning a sound insulator between the spacer members.

8. The method of claim 7 wherein the step of isolating includes positioning a sound insulator between the spacer members.

9. The method of claim 1 wherein the step of measuring includes detecting signals commensurate with echos produced upon reflection from the abnormality of said second longitudinal mode wave and employing such detected signals as a verification of the presence of the abnormality.

10. The method of claim 9 wherein the test object is a hollow member having substantially parallel inner and outer wall surfaces and wherein said first surface is the outer wall surface of the hollow member.

11. The method of claim 10 wherein the abnormality is a crack originating at the inner wall surface and wherein the propogated longitudinal mode wave is reflected from the tip of the crack and is the first serially received echo.

12. The method of claim 11 wherein the steps of transmitting and receiving each include spacing a piezoelectric crystal from the outer wall surface of the hollow member.

13. The method of claim 12 wherein the receiving piezoelectric crystal defines an axis which is oriented at an angle in the range of 12° to 28° relative to a line normal to the outer wall surface of the hollow member.

14. The method of claim 13 wherein the steps of spacing include mounting the piezoelectric crystals on members comprised of a material having low acoustic attenuation characteristics.

15. The method of claim 14 wherein the step of isolating includes positioning a sound insulator between the spacer members.

16. The method of claim 9 wherein the shear mode wave reflected from the second surface of the test object comprises said second longitudinal mode wave and a third mode converted wave which follows the second surface and wherein said method further comprises the steps of:

detecting signals commensurate with echos produced upon reflection from the abnormality of the third mode converted wave;

determining the time delay between receipt of echos produced upon reflection from the abnormality of said first longitudinal mode wave and said third mode converted wave, said time delay being indicative of the length of the abnormality in a direction generally transverse to the first surface of the test object.

* * * * *